US007498130B2

(12) United States Patent
Elmaleh

(10) Patent No.: US 7,498,130 B2
(45) Date of Patent: Mar. 3, 2009

(54) METHOD OF REDUCING VIRAL LOAD

(75) Inventor: David R. Elmaleh, Newton, MA (US)

(73) Assignee: Massachusetts General Hospital, Boston, MA (US)

( * ) Notice: Subject to any disclaimer, the term of this patent is extended or adjusted under 35 U.S.C. 154(b) by 158 days.

(21) Appl. No.: 11/176,577

(22) Filed: Jul. 7, 2005

(65) Prior Publication Data

US 2006/0035828 A1 Feb. 16, 2006

Related U.S. Application Data

(63) Continuation-in-part of application No. 10/436,872, filed on May 13, 2003.

(60) Provisional application No. 60/586,043, filed on Jul. 7, 2004.

(51) Int. Cl.
*C12Q 1/70* (2006.01)
*A61K 35/14* (2006.01)
*A61K 39/21* (2006.01)
*A61K 39/29* (2006.01)

(52) U.S. Cl. ............... 435/5; 530/380; 424/208.1; 424/228.1

(58) Field of Classification Search ............ None
See application file for complete search history.

(56) References Cited

U.S. PATENT DOCUMENTS

| | | | |
|---|---|---|---|
| 4,297,344 | A | 10/1981 | Schwinn et al. |
| 4,340,589 | A | 7/1982 | Uemura et al. |
| 4,388,232 | A | 6/1983 | Eibl et al. |
| 4,623,718 | A | 11/1986 | Collen |
| 5,989,593 | A | 11/1999 | Ideno et al. |
| 2002/0127698 | A1 | 9/2002 | Geiben Lynn et al. |

FOREIGN PATENT DOCUMENTS

| | | |
|---|---|---|
| EA | 0 355 905 | 8/1989 |
| JP | 63132843 | 4/1988 |
| WO | WO 99/58098 | 11/1999 |
| WO | WO-02/058638 | 8/2002 |
| WO | WO-02/058638 A2 | 8/2002 |
| WO | WO-2004/100973 A2 | 11/2004 |

OTHER PUBLICATIONS

Jay Levy, Trends in Immunology, 2003, 24(12):628-632.*
Geiben-Lynn et al., Journal of Biological Chemistry, 2002, 277(44):42352-42357.*
Belzar, K. J. et al., "The Effect of a Reducing-end Extension of Pentasaccharide Binding by Antithrombin", *Journ. of Bio. Chem.*, 275(12):8733-8741 (2000).
Brennan, S. O. et al., "Physiological variant of anthrombin-III lacks carbohydrate sidechain at Asn 135", *Fed. of Euro. Bio. Soc.*, 219(2):431-436 (Jul. 1987).
Carrell, R. W. et al., "Biological implications of a 3 Å structure of dimeric antithrombin", *Structure*, 2:257-270 (Apr. 15, 1994).

Carrell, R. W. et al., "Mobile Reactive centre of serpins and the control of thrombosis", *Nature*, 353:576-578 (Oct. 10, 1991).
Carrell, R. W. et al., "Mobile Reactive centre of serpins and the control of thrombosis", *Nature (Corrections)*, 364:737 (Aug. 19, 1993).
Collen, D. et al., *The Physiological Inhibitors of Blood Coagulation and Firbinolysis*, Jul. 22-23, 1978 Round-Table Conference at Univ. of Leuven, Belgium (1979).
Evans, D. L. et al., "Heparin Binding Site, Conformational Change, and Activation of Antithrombin", *Biochemistry*, 31:12629-12642 (1992).
Garzino-Demo, A., et al., "Spontaneous and antigen-induced production of HIV-inhibitory β-chemokines are associated with AIDS-free status", *PNAS*, 96(21):11986-11991 (Oct. 12, 1999).
Geiben-Lynn, R., Ph.D., "Anti-Human Immunodeficiency Virus Noncytolytic CD8+ T-Cell Response: A Review", *AIDS Patient Care and STDs*, 16(10):471-477 (2002).
Harper, J. L., M.D., "Antithrombin III Deficiency", *Medicine* (website—http://www.emedicine.com) (Oct. 31, 2001).
Hepatitis Foundation International (website—http://www.hepfi.org), "The ABCs of hepatitis." (Mar. 4, 2003).
Huntington, J. A. et al., "A 2.6 Å Structure of a Serpin Polymer and Implications for Conformational Disease," *J. Mol. Biol.*, 293:449-455 (1999).
Jacobi, J., "Pathophysiology of Sepsis," *AJHP*, 59(4)(1):S3-S8 (Feb. 12, 2002).
Jairajpuri, M. A. et al., "Antithrombin III Phenylalanines 122 and 121 Contribute to its High Affinity for Heparin and its Conformational Activation", *Amer. Soc. for Bioch. and Mol. Biol.*, 1-42 (Jan. 29, 2003).
Kurachi, K. et al., "Inhibition of Bovine Factor $IX_\alpha$ and Factor $X_{\alpha\beta}$ by Antithrombin III", *Biochemistry*, 15(2):373-377 (1976).
Levy, J. H., M.D. et al., "Recombinant Antithrombin: Production and Role in Cardiovascular Disorder", *Seminars in Thrombosis and Hemostasis*, 27(4):405-416 (2001).
Mourey, L. et al., "Crystal Structure of Cleaved Bovine Antithrombin III at 3·2 Å Resolution", *J. Mol. Biol.*, 232:223-241 (1993).
Nordenman, B. et al., "The Size and Shape of Human and Bovine Antithrombin III", *Eur. J. Biochem.*, 78:195-203 (1977).
O'Reilly, M. S. et al., "Antiangiogenic Activity of the Cleaved Conformation of the Serpin Antithrombin", *Science*, 285:1926-1928 (Sep. 17, 1999).
Rosenberg, R. D. et al., "The Purification and Mechanism of Action of Human Antithrombin-Heparin Cofactor", *Journ. of Biol. Chem.*, 248(18):6490-6505 (Sep. 23, 1973).

(Continued)

*Primary Examiner*—Stacy B Chen
(74) *Attorney, Agent, or Firm*—Beth E. Arnold, Esq.; Foley Hoag LLP

(57) ABSTRACT

Methods of activating ATIII in situ in a blood product are disclosed, as is the use of such methods and blood products in treating infectious diseases, inflammatory disorders and diseases or conditions that are mediated by thrombin activation.

10 Claims, 2 Drawing Sheets

OTHER PUBLICATIONS

Rublee, D. et al., "Quality of Life Effects of Antithrombin III in Sepsis Survivors: Results From the KyberSept Trial [ISRCTN22931023]", *Critical Care*, 6:349-356 (Jun. 24, 2002).

Schreuder, H. A. et al., "The Intact and Cleaved Human Antithrombin III Complex as a Model for Serpin-Proteinase Interactions", *Structural Biol.*, 1(1):48-54 (Jan. 1994).

Skinner, R. et al., "Implications for Function and Theraphy of a 2.9Å Structure of Binary-complexed Antithrombin", *J. Mol. Biol.*, 283:9-14 (1998).

Souter, P. J. et al., "Antithrombin inhibits lipopolysaccharide-induced tissue factor interleukin-6 production by mononuclear cells, human umbilical vein endothelial cells, and whole blood", *Crit. Care Med.*, 29(1):134-139 (2001).

Warren, B. L. M.D., et al., "High-Dose Antithrombin III in Severe Sepsis", *JAMA*, 286(15):1869-1878 (Oct. 17, 2001).

International Search Report mailed on Feb. 8, 2005.

Bayer Corporation, Thrombate III, Antithrombin II (Human) data sheet, last revised. pp. 1-7 (2001).

Coombe, D. R. et al., "Low Anticoagulant Heparin Retains Anti-HIV Type 1 Activity in Vitro", *AIDS Research and Human Retroviruses*, 11(11):1393-1396 (Mary Ann Liebert, US)(1995).

Geiben-Lynn, R. et al., "Purification of a Modified Form of Bovine Antithrombin III as an HIV-1 $CD8^+$ T-Cell Antiviral Factor", *Journ. of Biol. Chem.*, 277(44):42352-42357 (Amer. Soc. of Biochem. Biologists, Birmingham, US)(Nov. 1, 2002).

International Search Report dated Dec. 19, 2005.

Supplementary Partial European Search Report dated Aug. 29, 2007.

* cited by examiner

Heparin activity is due to BSA in the incubation sample. This activity decreases after day nine and is zero on day 12.

METHOD OF REDUCING VIRAL LOAD

RELATED APPLICATIONS

This application claims priority to provisional application U.S. Ser. No. 60/586,043, filed Jul. 7, 2004 and is a continuation-in-part of U.S. Ser. No. 10/436,872, filed May 13, 2003, the content of which applications are specifically incorporated herein by reference in their entireties.

BACKGROUND OF THE INVENTION

Although vaccines are available to prevent many types of viral infection, not all viruses are able to be prevented by a vaccine and not all potential victims are able to receive vaccinations even if they are available. For example, the retrovirus human immunodeficiency virus (HIV) causes Acquired Immunodeficiency Syndrome (AIDS), an incurable disease for which there is no vaccine in which the body's immune system breaks down leaving the victim vulnerable to opportunistic infections, e.g., pneumonia, and certain cancers, e.g., Karposi's Sarcoma. Many patients with HIV are co-infected with Hepatitis C Virus (HCV), Hepatitis B (HBV), or other viruses. Although a vaccine is available for certain viruses such as HBV, many at-risk people do not receive or have access to the vaccine. Further, some data indicate that the HBV vaccine is not as effective in people already infected with HIV.

Viral infections, once established, are generally incurable. There are, however, a variety of anti-viral drugs that can prevent viruses from reproducing and ravaging the body's immune system, i.e., that slow the infection and lengthen the subject's life. However, such therapies often only partially effective, and it is unknown how much viral suppression is required to achieve durable virologic, immunologic, and clinical benefits. Anti-viral drugs are often highly toxic and can cause serious side effects, including heart damage, kidney failure, and osteoporosis.

For example, highly active antiretroviral drug therapy (HAART) is a widely used anti-HIV therapy that entails multiple-drug protease inhibitor-containing regimens that can completely suppress viral replication. Hepatic injury is a major concern as a result of antiretroviral therapy (HAART) and has been shown to occur with all classes of antiretroviral therapy. The efficacy of current anti-HIV therapy is further limited by the complexity of regimens, pill burden, and drug-drug interactions. Compliance with the toxic effects of antiretroviral drugs make a lifetime of combination therapy a difficult prospect and many patients cannot tolerate long-term treatment with HAART. Further, poor adherence to combination therapy regimes has led to the emergence of drug-resistant strains of HIV.

There is clearly a need for new anti-viral agents and other novel approaches to treating viral infection.

SUMMARY OF THE INVENTION

The present invention is based on the surprising finding that ATIII may be activated using saccharides such as heparin directly in situ in a blood product, such as blood, plasma, serum albumin, recombinant plasma, and the like, ad re-administered to a subject. For example, a blood product of a subject may be incubated with heparin or other saccharide, dialyzed, and re-administered into the subject. Alternatively, a blood product from another source, such as a commercial source, may be incubated with heparin or other saccharide, dialyzed, and administered to a subject. The blood products so treated contain activated ATIII in an effective dose to treat viral infection. This novel treatment eliminates the need for activated ATIII preparation in advance. Such treated blood products as a treatment may be useful, for example, in treating patients having viral infections or diseases or conditions that are caused by or contributed to by thrombin activation. The methods of treatment provided by the present invention may result in shorter pre-clinical and clinical testing times. Further, these methods of treatment provide an alternative, or supplement, to existing treatment methods of viral infection using purified activated ATIII pharmaceutical preparations.

Other features and advantages of the invention will become apparent from the following detailed description and claims.

DETAILED DESCRIPTION OF THE INVENTION

1. Definitions

Figure 1:
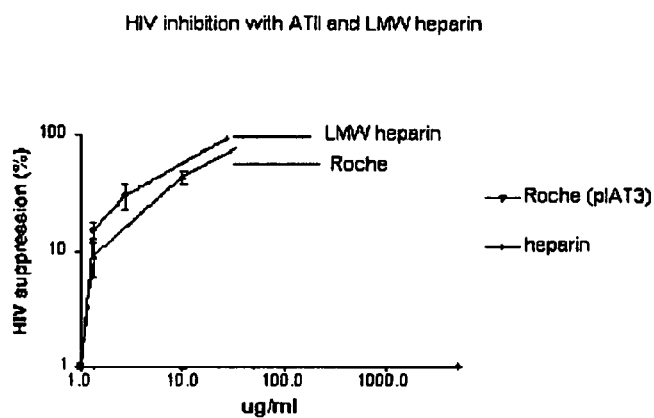
FIG. 1 depicts the HIV-1 inhibitory activity in blood treated with LMW heparin (as described below in Example 4).
Figure 2:
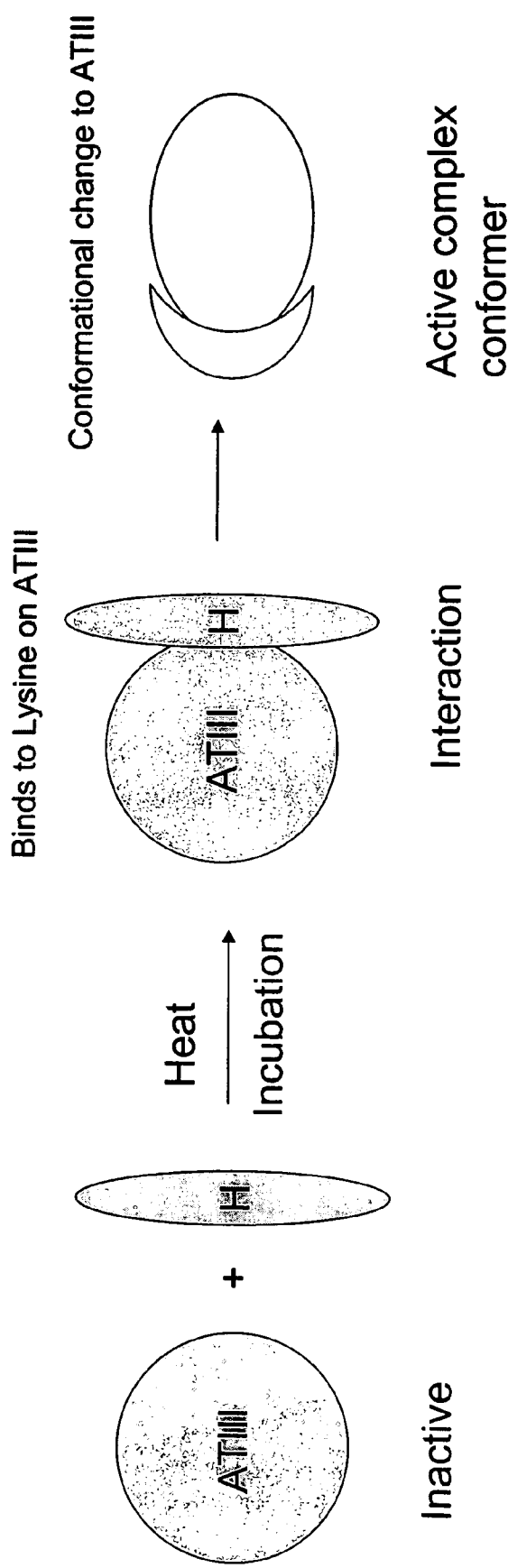
FIG. 2 depicts the mechanism of action of activated heparin. Pure ATIII from Aventis (human source) and from GTC (recombinant) are inactive. Oligosaccharide and ATIII incubation and/or incubation with heat accelerate the interaction of these molecules to form a complex that undergoes a conformational change to produce an active form.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "activating ATIII" or "to activate ATIII" refers to treating ATIII under suitable conditions such that the ATIII becomes high molecular weight ATIII and is able to reduce viral load, i.e., "activated ATIII."

The term "administering" includes any method of delivery of a pharmaceutical composition or therapeutic agent into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "ATIII" refers to antithrombin III.

The term "blood product" refers to any product or substance that is blood or is derived from blood. For example, blood products include, but are not limited to, whole blood, plasma, serum, serum albumin preparations, and artificial preparations of the same, such as recombinant plasma.

The term "mammal" is known in the art, and exemplary mammals include humans, primates, bovines, porcines, canines, felines, and rodents (e.g., mice and rats).

The term "high molecular weight ATIII" means ATIII that has been treated to increase the molecular weight of the molecule relative to wildtype ATIII, e.g. to about 60 Kda to about 240 kDa from 58 kDa.

A "patient," "subject" or "host" to be treated by the subject method may mean either a human or non-human animal.

The phrase "pharmaceutically acceptable" refers to those compositions and dosages thereof within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. The term "pharmaceutically acceptable carrier" refers to a carrier(s) that is "acceptable" in the sense of being compatible with the other ingredients of a composition and not deleterious to the recipient thereof. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "saccharide" includes both monosaccharides and polysaccharides.

The term "a saccharide able to activate ATIII" refers to any saccharide able to transform wildtype ATIII into activated and/or high molecular weight ATIII that has the ability to reduce viral load.

The term "therapeutically effective amount" refers to that amount of activated ATIII, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treating" as used herein is intended to encompass curing as well as ameliorating at least one symptom or the progression of any condition or disease. decreased or prevented. Treatment may be performed either prophylactically, or subsequent to the initiation of a pathologic event.

The term "viral load" refers to the concentration of a virus, such as HIV, in the blood.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

2. In Situ Blood Activation of ATIII

Antithrombin III (ATIII) is a glycoprotein present in blood plasma with a well-defined role in blood clotting. Specifically, ATIII is a potent inhibitor of the reactions of the coagulation cascade with an apparent molecular weight of between 54k Da and 65 kDa (Rosenberg and Damus, J. Biol. Chem. 248: 6490-505 (1973); Nordenman et al., Eur. J. Biochem., 78: 195-204 (1977); Kurachi et al., Biochemistry 15: 373-7 (1976)), of which some ten percent is contributed by four glucosamine-base carbohydrate chains (Kurachi et al., Biochemistry 15: 373-7 (1976); Petersen et al., in The Physiological Inhibitors of Coagulation and Fibrinolysis (Collen et al., eds) Elsevier, Amsterdam, p. 48 (1979)).

Although its name implies that it works only on thrombin, ATIII actually serves to inhibit virtually all of the coagulation enzymes to at least some extent. The primary enzymes it inhibits are factor Xa, factor IXa, and thrombin (factor Ia). It also has inhibitory actions on factor XIIa, factor Xia and the complex of factor VIIa and tissue factor but not factor VIIa and activated protein C. ATIII also inhibits trypsin, plasmin and kallikrein (Charlotte and Church, Seminars in Hematology 28:3-9 (1995). Its ability to limit coagulation through multiple interactions makes it one of the primary natural anticoagulant proteins.

ATIII acts as a relatively inefficient inhibitor on its own. However, ATIII can be activated by a simple template mechanism, or by an allosteric conformational change brought about by heparin binding (Skinner et al., J. Mol. Biol. 283: 9-14 (1998); Huntington et al., J. Mol. Biol., 293: 449-55 (1999); Belar et al., J. Mol. Biol. Chem., 275: 8733-41 (2000)). When ATIII binds heparin, the speed with which the reaction that causes inhibition occurs is greatly accelerated. This interaction is the basis of heparin based anticoagulation therapies.

Pure plasma derived or recombinant ATIII is inactive in lowering HIV viral loads. However, we have shown in U.S. Ser. No. 10/436,872 that ATIII that has been treated to have a higher molecular weight, or "activated," effectively reduces HIV viral loads in infected cells. This application, which is hereby incorporated by reference in its entirety, features pharmaceutical compositions comprising high molecular weight antithrombin III (ATIII) in an amount effective to treat a retroviral infection. Incubation of the ATIII with heparin and/or heat in a variety of combinations was shown to activate the ATIII and inhibit proliferation of the retroviral infection.

The present invention is based on the surprising finding that ATIII may be activated using saccharides such as heparin directly in situ in a blood product, such as blood, plasma, serum albumin, recombinant plasma, and the like. The blood product so treated contains activated or high molecular weight ATIII. This novel treatment eliminates the need for advance ATIII preparation, e.g. preparation, purification and formulation into a pharmaceutical composition. Such a treatment may be useful, for example, in treating patients having viral disease or diseases or conditions that are caused by or contributed to by thrombin activation.

For example, the patient's own blood or plasma or serum albumin in combination with heparin may be incubated at moderate conditions (about 37 to about 40° C.), (not necessary if the saccharide concentration is much lower than the ATIII equimolar concentration in the treated blood), and the activated blood product injected back into the patient. The rationale behind this idea is that most patients will have between about 100 to about 150 mg ATIII per liter of blood, for which only a low heparin quantity is needed for activation.

Accordingly, a method for preparing activated ATIII in situ in a blood product may comprise: (a) adding to a blood product comprising ATIII a saccharide able to activate ATIII in an amount sufficient to activate said ATIII; and (b) incubating the resulting mixture of the blood product and saccharide under conditions sufficient to activate said ATIII. In certain embodiments, the saccharide may be added in a quantity in excess of that quantity of ATIII in the blood product, for example, in an about 0.1 to about 1.0 equimolar amount of the quantity of ATIII in the blood product.

The conditions sufficient to activate the ATIII are, in certain embodiments about 37° C. to about 40° C. for about 24 to about 72 hours. In certain embodiments, the temperature is about 37° C. to about 38° C., about 38° C. to about 39° C. or about 39° C. to about 40° C. In certain embodiments, the incubation time is about 24 to about 36 hours, about 36 to about 48 hours, about 48 to about 60 hours, or about 60 to about 72 hours.

The blood product may be any product or substance that is blood or is derived from blood. For example, blood products include, but are not limited to, whole blood, plasma, serum, serum albumin preparations, and artificial preparations of the same, such as recombinant plasma.

The saccharide, may be for example, an oligosaccharide, such as any form of heparin, including low molecular weight heparin (about 2 to about 4 kDa), high molecular weight heparin (at least 12 kDa), and standard unfractionated heparin. In certain embodiments, the saccharide is a pentasaccharide. Further, the saccharide may be an oligosaccharide treated by a glycosidase or other restriction enzyme. In certain embodiments, the saccharide may be added in an about a 0.1 to about 0.2, about 0.2 to about 0.3, about 0.3 to about 0.4, about 0.4 to about 0.5, about 0.5 to about 0.6, about 0.6 to about 0.7, about 0.7 to about 0.8, about 0.8 to about 0.9, or about 0.9 to about 1.0 equimolar amount of the quantity of ATIII in the blood product. Saccharides that may be used in the methods of the present invention include, but are not limited to, monosaccharides, disaccharides, and polysaccharides (including penta-, hepta- and hexa-saccharides), sugar alcohols, and amino sugars. Examples of monosaccharides include glucose, fructose, galactose, mannose, arabinose, and inositol. Examples of disaccharides include saccharose, lactose, maltose, pectin. Examples of sugar alcohols include mannitol, sorbitol, and xylitol. Examples of amino sugars include glucosamine, galactosamine, N-acetyl-D-glucosamine and N-acetyl galactosamine, which are the building blocks that can form more complex oligosaccharides, such as aminoglycosides and heparin. In certain embodiments, the oligosaccharides may be low molecular weight (2-4 kDa) heparin, high molecular weight (at least 12 kDa) heparin, standard unfractionated heparin, pectin, pentasaccharides, and aminoglycosides. In certain embodiments, the oligosaccharide has an affinity for ATIII. Saccharides as used herein can be derivatized with additional small molecules, such as biotin, avidin or streptavidin. Saccharides in certain embodiments may be sulfated oligosaccharides or oligosaccharides identified by glycosidase and other restriction enzyme reactions.

Blood products in which ATIII has been activated in situ are also within the scope of the present invention. Such blood products may be packaged, for example, in sterile i.v. or incubation bags.

3. Methods of Treating

The above-described methods of treating blood products to activate ATIII in situ and activated blood products produced thereby may be incorporated into methods of treating a disease in a subject. In certain embodiments, such methods of treating a disease in a subject in need of treatment may comprise (a) adding to a blood product comprising ATIII a saccharide able to activate ATIII in an amount sufficient to activate said ATIII; (b) incubating the resulting mixture of the blood product and saccharide under conditions sufficient to activate said ATIII; and (c) administering said mixture into said subject to treat a disease. Such methods may, in certain embodiments, further comprise purifying said mixture to remove unreacted saccharide prior to the infusing step, e.g. by dialysis. The methods of the present invention can be used to human and animal subjects such as cows, horses, dogs, cats, etc.

In certain embodiments, the disease is caused by a bacteria or virus. Exemplary viruses that may be treated using the methods of activating ATIII in situ or with the blood products of the invention include Hepatitis A Virus (HAV) infection, Hepatitis B Virus (HBV) infection, Hepatitis C Virus (HCV) infection, Human Immunodeficiency Virus (HIV) infection, corona virus infection, cytomegalovirus infection (CMV) and severe acute respiratory syndrome (SARS). In certain embodiments, the virus is a retrovirus, such as HIV. In other embodiments, the disease may be a disease or condition that is caused by or contributed to by thrombin activation.

Thrombin activation related diseases in a patient include sepsis, trauma, acute respiratory distress syndrome, thrombosis, stroke, and restenosis. The methods may also be used to treat patients at risk of a thrombin related pathological disease such as reocclusion and restenosis in percutaneous transluminal coronary angioplasty; thrombosis associated with surgery, ischemia/reperfusion injury; and coagulation abnormalities in cancer or surgical patients. The treated blood product administered in the methods may serve an anti-coagulant in the treatment of, for example, congenital antithrombin III deficiency which leads to an increased risk of venous and arterial thrombosis, or acquired antithrombin III deficiency which results in disseminated intravascular coagulation, microangiopathic hemolytic anemias due to endothelial damage (i.e. hemolytic-uremic syndrome) and veno-occlusive disease (VOD). The methods and blood products may also be used to treat semi-chronic diseases like arterial thrombus and deep vein thrombosis.

Both methods of treating that are single-dose administrations and longer term, chronic, multi-dose treatments are within the scope of the present invention.

In certain embodiments, the methods of treating may further comprise administering other pharmaceutical compositions, such as an anti-viral drug, to said subject. For example, in certain embodiments, an anti-viral drug may be administered concurrently with the blood product. In other embodiments, however, an anti-viral drug may be administered subsequent to administering the mixture. In still other embodiments, anti-viral drug may be administered both concurrently and subsequently with the blood product. An anti-viral drug may be added to the mixture, or administered as a separate composition.

Exemplary anti-viral drugs include reverse transcriptase inhibitors such as zidovudine, zalcitabine, didanosine, stavudine, lamivudine, abacavir, tenofovir, nevirapine, efavirenz, delavirdine; protease inhibitors such as saquinavir, ritonavir, indinavir, nelfinavir, amprenavir, lopinavir, and other agents such as adenine arabinoside, adenine arabinoside 5'-monophosphate, acyclovir, ganciclovir, famciclovir, lamivudine, clevudine, afedovir dipivoxil, entecavir, IFN-a-2b, IFN-a-2a, lymphoblastoid IFN, consensus-IFN, IFN-b, IFN-g, pegylated IFN-a-2a, corticosteroids, or thymosin al, IL-2, IL-12, ribavirin, cyclosporin or granulocyte macrophage colony stimulating factor, fusion inhibitors such as T-20 (enfuvirtide), zinc finger inhibitors, and ribavrin.

Highly Active Antiretroviral Therapy (HAART) is a recommended treatment for HIV and other viral infections. HAART combines two or more anti-viral medications in a daily regimen, also known as a "cocktail." Cocktails of anti-viral drugs are well-known to those of skill in the art. For example, effective known anti-HIV cocktails include, but are not limited to, combinations such as AZT, 3TC and efavirenz; nevirapine, stavudine and lamivudine; emtricitabine and tenofovir disoproxil fumarate; indinavir, zidovudine and lamivudine (3TC); and zidovudine and 3TC. An effective anti-HCV cocktail is ribavrin and interferon.

The combined use of blood products of the present invention and other anti-virals may reduce the required dosage for any individual component because the onset and duration of effect of the different components may be complimentary. In such combined therapy, the different active agents may be delivered together or separately, and simultaneously or at different times within the day.

Other pharmaceutical compositions that may be administered either concurrently, subsequently, or both concurrently and subsequently include ATIII and interferon or interferon derived drugs. For example, the blood product may be supplemented with additional ATIII prior to adding the oligosaccharide to activate it. In another embodiment, anticoagulants may be used alone or in combination with saccharides such as heparin or a pentasaccharide to treat the blood products of the invention prior to their use in a treatment method in order to improve their efficacy.

Further, high molecular weight ATIII pharmaceutical compositions as described in Pending U.S. patent application Ser. No. 10/436,872 may be used to supplement the method of treatment, e.g. by administering it either concurrently, subsequently, or both concurrently and subsequently with administration of the treated blood products.

The blood products of the present invention may be administered directly to a subject or may be formulated in a conventional manner using one or more physiologically acceptable carriers or excipients. For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. The blood product may be formulated for parenteral administration by injection, e.g., by bolus injection or continuous infusion. For injection, the blood products of the invention can be formulated in liquid solutions, preferably in physiologically compatible buffers such as Hank's solution or Ringer's solution. In addition, the blood products may be formulated in solid form and redissolved or suspended immediately prior to use. Lyophilized forms of the blood products are also included.

Formulations for injection may be presented in unit dosage form, e.g., in ampoules or in multi-dose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Furthermore, as those skilled in the art will understand, the dosage of any blood product, agent, compound, drug, etc. used in the methods of the present invention will vary depending on the symptoms, age and body weight of the patient, the nature and severity of the disorder to be treated or prevented, the route of administration, and the form of the supplement. Any of the subject formulations may be administered in any suitable dose, such as, for example, in a single dose or in divided doses. Dosages for the blood products of the present invention, alone or together with any other compound of the present invention, or in combination with any compound deemed useful for the particular disorder, disease or condition sought to be treated, may be readily determined by techniques known to those of skill in the art, based on the present description, and as taught herein. Also, the present invention provides mixtures of more than one subject compound, as well as other therapeutic agents.

ATIII has been shown to be well-tolerated when administered at a dose of ~100 U/kg/day (Warren et al., *JAMA* 286: 1869-78 (2001)) and has an overall elimination half-life with 18.6 h was demonstrated (Ilias et al. Intensive Care Medicine 26: 7104-7115 (2000)). While the dose is appropriately determined depending on symptom, body weight, sex, animal species and the like, it is generally 1-1,000 units/kg body weight/day, preferably 10-500 units/kg body weight/day of ATIII (as contained in the treated blood products of the invention) for a human adult, which is administered in one to several doses a day. In the case of intravenous administration, for example, the dose is preferably 10-100 units/kg body weight/day.

The precise time of administration and amount of any particular product or compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing. In certain embodiments, the administration regimen may also be dependent on the relative amount of ATIII in the blood product, for example, when the blood product is the patient's blood.

While the subject is being treated, the health of the patient may be monitored by measuring one or more relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations. In embodiments wherein the blood products are administered along with a HAART regimen, the blood products may be administered in the HAART rest interval.

Treatment may be initiated with smaller dosages which are less than the optimum dose of the product or compound. Thereafter, the dosage may be increased by small increments until the optimum therapeutic effect is attained.

4. Kits

The present invention also provides kits comprising compositions of the present invention, and optionally instructions for their use. For example, kits for the practice of certain of the treatment methods of the invention may comprise a saccharide able to activate ATIII and instructions for use. Still other kits for the practice of certain of the treatment methods of the invention may comprise blood products in which ATIII has been activated in situ. Further, the present invention provides kits for the methods of preparing activated ATIII in situ in a blood product. For example, such kits may comprising an oligosaccharide able to activate ATIII and instructions for use.

Kit components may be packaged for either manual or partially or wholly automated practice of the foregoing methods. In other embodiments involving kits, this invention contemplates a kit including compositions of the present invention, and optionally instructions for their use. In other embodiments, a kit may further comprise controls, reagents, buffers, and/or instructions for use. Such kits may have a variety of uses, including, for example, imaging, diagnosis, therapy, and other applications.

Exemplification

The invention now being generally described, it will be more readily understood by reference to the following examples, which are included merely for purposes of illustration of certain aspects and embodiments of the present invention, and are not intended to limit the invention.

EXAMPLE 1

Preparation Procedures for In Vitro Plasma ATIII Activation Using Standard, Unfractionated Heparin Standard, unfractionated heparin for human use (1,000-10,000 units, or about 2 to about 40 mg) was added to 500 mL samples of commercially available human plasma (containing an average of about 120 to about 150 mg of ATIII) in a sterile incubation bag. The amount of heparin added to the bag depends on the viral load of the patient and the treatment regimen desired. The resulting mixture was incubated at room temperature, 37° C. or 40° C., for 24-72 hours. Gentle mixing was applied as necessary during the incubation period. The incubated mixture may be infused into a patient with or without further purification to remove unreacted heparin. In these procedures, the heparin dosage is very low compared to the level of ATIII in the plasma so that free heparin in the resultant mixture is avoided, thus decreasing the risk for bleeding.

EXAMPLE 2

Preparation Procedures for In Vitro Blood ATIII Activation Using Standard, Unfractionated Heparin Standard, unfractionated heparin for human use (1,000-20,000 units, or about 2 to about 40 mg) was added to 1,000 mL samples of blood drawn from HIV or HCV patients (containing an average of about 70 to 150 mg of ATIII) in a sterile incubation bag. The resulting mixture was incubated at room temperature, 37° C. or 40° C., for 24-72 hours. Gentle mixing was applied as necessary during the incubation period. The incubated mixture may be infused into a patient with or without further purification to remove unreacted heparin. In these procedures, the heparin dosage is very low compared to the level of ATIII in the plasma so that free heparin in the resultant mixture is avoided, thus decreasing the risk for bleeding.

EXAMPLE 3

Preparation Procedures for In Vitro Plasma ATIII Activation Using Low Molecular Weight Heparin Low molecular weight (LMW) heparin for human use (1,000-10,000 units, or about 2 to about 20 mg) was added to 500 mL samples of commercially available human plasma (containing an average of about 70 to about 150 mg of ATIII) in a sterile incubation bag. The resulting mixture was incubated at room temperature, 37° C. or 40° C., for 24-72 hours. Gentle mixing was applied as necessary during the incubation period. The incubated mixture may be infused into a patient with or without further purification to remove unreacted heparin. In these procedures, the heparin dosage is very low compared to the level of ATIII in the plasma so that free heparin in the resultant mixture is avoided, thus decreasing the risk for bleeding.

EXAMPLE 4

Preparation Procedures for In Vitro Blood ATIII Activation Using Low Molecular Weight Heparin Low molecular weight (LMW) heparin for human use (1,000-20,000 units, or about 2 to 20 mg) was added to 1,000 mL samples of blood drawn from HIV or HCV patients (containing an average of about 70 to 150 mg of ATIII) in a sterile incubation bag. The resulting mixture was incubated at room temperature, 37° C. or 40° C., for 24-72 hours. Gentle mixing was applied as necessary during the incubation period. The incubated mixture may be infused into a patient with or without further purification to remove unreacted heparin. In these procedures, the heparin dosage is very low compared to the level of ATIII in the plasma so that free heparin in the resultant mixture is avoided, thus decreasing the risk for bleeding.

EXAMPLE 5

Activation of ATIII in the Blood or Blood Plasma Using Heparin, Heparin Derivatives, or Other Oligosaccharides Able to Activate ATIII ATIII may also be activated in the blood or blood plasma using the protocols described in Examples 1-4 above using a 0.1 to 1.0 equimolar amount of any heparin-derived pentasaccharide or other oligosaccharide able to activate ATIII. Examples of such are provided in the Detailed Description above.

EXAMPLE 6

Estimation of Protein Bound Heparin and Free Heparin in Modified Forms

To estimate the free heparin and protein-bound heparin, both UV and refractive index (RI) integrations were used as follows.

To correct for the differences in the absorption detection by both UV and RI detectors, a correction coefficient was established from a pure protein standard measure with both detectors according to the following formula:

$$K=UV_{protein}/RI_{protein} \text{ or } RI_{protein}=UV_{protein}/K$$

The total RI integration may be expressed as follows:

$$RI_{total}=RI_{protein}+RI_{heparin}$$

Therefore, the bound heparin ($B_{heparin}$) is $$\% B_{heparin}=[(RI_{total}-UV_{protein}/K)/RI_{total}]\times100$$

Free heparin ($F_{heparin}$) is calculated according to:

$$\% F_{heparin}=[F_{heparin}/(F_{heparin}+B_{heparin})]\times100$$

EXAMPLE 7

Assay for Inhibition of HIV-1 Replication

X4 HTLV-IIIB (hereinafter X4 HIV; Chang et al., NATURE, 363: 466-9 (1993)), a prototypical T-tropic strain of HIV (American Type Tissue Collection, Monassass, Va., USA; ATCC No. CRL-8543), was used to assess the effect of the ATIII activation protocols on T-tropic HIV infection. The quantity of virus in a specified suspension volume (e.g. 0.1 ml) that will infect 50% of a number (n) of cell culture microplate wells, or tubes, is termed the Tissue Culture Infectious Dose 50 [$TCID_{50}$]. $TCID_{50}$ is used as an alternative to determining virus titer by plaqueing (which gives values as PFUs or plaque-forming units). Human T lymphoblastoid cells (H9 cells) expressing the human leukocyte antigen proteins (HLA) B6, Bw62, and Cw3 were acutely infected with X4 HIV at a MOI of $1\times10^{-2}$ $TCID_{50}$ per milliliter. The infected H9 cells were resuspended to $5\times10^5$ cells/ml in R20 cell culture medium. Two milliliters of this suspension was pipetted into each well of a 24-well microtiter plate. These cells were then cultured in the presence or absence of samples having activated ATIII for up to 12 days. Every three days (days 3, 6, 9 and 12), 1 ml cell supernatant was removed from test wells and replaced with an equal volume of R20 cell culture medium. Control wells were similarly sampled but received media containing samples that were untreated.

The concentration of the viral core protein p24 (gag) for HIV (Alliance® HIV-1 p24 ELISA kit, NEN® Life Science, Boston Mass., USA) was measured for each sample obtained at days 0, 3, 6, 9 and 12 respectively.

The results which are shown in FIG. 1 demonstrate HIV-1 inhibitory activity in blood treated with LMW heparin.

Equivalents

While specific embodiments of the subject invention have been discussed, the above specification is illustrative and not restrictive. Many variations of the invention will become apparent to those skilled in the art upon review of this specification and the claims below. For example, variants on the quantities of reactants given in the above Examples are within the scope of the invention, as are variants on the incubation time. The full scope of the invention should be determined by reference to the claims, along with their full scope of equivalents, and the specification, along with such variations.

All publications and patents mentioned herein, including those listed below, are hereby incorporated by reference in their entirety as if each individual publication or patent was specifically and individually indicated to be incorporated by reference. In case of conflict, the present application, including any definitions herein, will control.

Wright, BIOASSAY, 18: 453-64 (1996); Skinner et al., J. Mol. Biol. 283: 9-14 (1998); Huntington et al., J. Mol. Biol. 293: 449-55 (1999); Deeks, JAMA, 286: 224-6 (2001); Stephenson, JAMA, 277: 614-6 (1997); Carr et al., Lancet, 351: 1881-3 (1998)

I claim:

1. A method of reducing viral load in a subject comprising:
   (a) adding to a blood product comprising ATIII a saccharide able to activate ATIII in an amount sufficient to activate said ATIII;
   (b) incubating the resulting mixture of the blood product and saccharide under conditions sufficient to activate said ATIII; and
   (c) administering said mixture and an anti-viral drug into said subject;
   wherein said saccharide is low molecular weight heparin; said low molecular weight heparin is added in a 0.1-1.0 equimolar amount of the quantity of said ATIII in said blood product; and said subject has one or more viral infections selected from the group consisting of Hepatitis C Virus (HCV) infection and Human Immunodeficiency Virus (HIV) infection.

2. The method of claim 1, wherein said conditions sufficient to activate said ATIII are about 37° C. to about 40° C. for about 24 to about 72 hours incubation.

3. The method of claim 1, wherein said blood product is blood plasma or HSA.

4. The method of claim 1, further comprising the step of purifying said mixture to remove unreacted saccharide prior to said administering step.

5. The method of claim 1, wherein said infection is a Human Immunodeficiency Virus (HIV) infection.

6. The method of claim 1, wherein said administering of said anti-viral drug is concurrent with said administering of said mixture.

7. The method of claim 1, wherein said administering of said anti-viral drug is subsequent to said administering of said mixture.

8. The method of claim 1, wherein said anti-viral drug is added to said resultant mixture before administration to said subject.

9. The method of claim 1, further comprising supplementing said blood product with additional ATIII prior to adding said saccharide.

10. The method of claim 1, wherein said anti-viral drug is an interferon or interferon derived drug.

* * * * *